(12) United States Patent
Khandelwal et al.

(10) Patent No.: US 9,857,376 B2
(45) Date of Patent: Jan. 2, 2018

(54) ONE POT PROCESS FOR THE PREPARATION OF GOLD QUANTUM CLUSTERS

(71) Applicant: COUNCIL OF SCIENTFIC AND INDUSTRIAL RESEARCH, New Delhi (IN)

(72) Inventors: Puneet Khandelwal, Pune (IN); Dheeraj Kumar Singh, Pune (IN); Pankaj Poddar, Pune (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/779,197

(22) PCT Filed: Mar. 24, 2014

(86) PCT No.: PCT/IN2014/000183
§ 371 (c)(1),
(2) Date: Sep. 22, 2015

(87) PCT Pub. No.: WO2014/147649
PCT Pub. Date: Sep. 25, 2014

(65) Prior Publication Data
US 2016/0054328 A1 Feb. 25, 2016

(30) Foreign Application Priority Data
Mar. 22, 2013 (IN) .......................... 0866/DEL/2013

(51) Int. Cl.
*G01N 33/58* (2006.01)
*C12Q 1/68* (2006.01)
(Continued)

(52) U.S. Cl.
CPC ............ *G01N 33/588* (2013.01); *B82Y 15/00* (2013.01); *C09K 11/06* (2013.01); *G01N 33/553* (2013.01); *C09K 2211/10* (2013.01)

(58) Field of Classification Search
CPC ........ G01N 33/585; C12Q 1/68; C09K 11/06; B82Y 15/00
See application file for complete search history.

(56) References Cited

U.S. PATENT DOCUMENTS 1,869,834 A 8/1932 Yoshioka
2014/0024026 A1* 1/2014 Alocilja ............. G01N 33/5434
435/6.11

FOREIGN PATENT DOCUMENTS

DE 27821 A 3/1964
KR 20040060357 7/2014

OTHER PUBLICATIONS

Zheng. Highly Fluorescent,Water-Soluble, Size-Tunable Gold Quantum Dots. Physical Review Letters vol. 93, No. 7 Aug. 13, 2004 p. 077402-01-077402-04.*

(Continued)

*Primary Examiner* — Matthew E Hoban
(74) *Attorney, Agent, or Firm* — Andrews Kurth Kenyon LLP

(57) ABSTRACT

The invention disclosed herein provides tunable process for the preparation of water dispersive, biocompatible, fluorescent L-cysteine labeled gold (Au) quantum clusters without using any toxic reactants. Further the invention discloses application of synthesized fluorescent gold (Au) quantum clusters in the field of nano-medicine, fluorescence imaging and florescence based sensors.

10 Claims, 2 Drawing Sheets

(51) Int. Cl.
    *C09K 11/06* (2006.01)
    *B82Y 15/00* (2011.01)
    *G01N 33/553* (2006.01)

(56) References Cited

OTHER PUBLICATIONS

International Search Report in PCT/IN2014/000183, mailed Sep. 17, 2014.
Deckert-Gaudig, Tanja et al., "Ultraflat Transparent Gold Nanoplates—Ideal Substrates for Tip-Ehanced Raman Scattering Experiments," SMALL, vol. 5, No. 4, 2009, pp. 432-436.
Donati, A. et al., "The effect of cysteine on electrodeposition of gold nanoparticle," Materials Science and Engineering B., vol. 176, No. 16, 2011, pp. 1307-1312 (XP02822374).
International Preliminary Report on Patentability in PCT/IN2014/000183, issued Sep. 22, 2015.
International Search Report in PCT/IN2014/000183, dated Sep. 17, 2014.
Deckert-Gaudig, Tanja et al., "Ultraflat Transparent Gold Nanoplates-Ideal Substrates for Tip-Ehanced Raman Scattering Experiments," SMALL, vol. 5, No. 4, 2009, pp. 432-436.
Dolati, A. et al., "The effect of cysteine on electrodeposition of gold nanoparticle," Materials Science and Engineering B., vol. 176, No. 16, 2011, pp. 1307-1312 (XP02822374).
Han et al., "Electrocatalysis of L-cysteine/laccase modified nanogold cathode for oxygen reduction," STN database accession No. 2012:22015 abstract & Yingyong Huaxue, vol. 28, No. 12, 2011, pp. 1421-1428 (XP00272743). Abstract.
Lan, H. et al., "Facile synthesis of gold nanoribbons by L-cysteine at room temperature," Database Inspec [online] The Institution of Electrical Engineers, Stevenanage, GB; May 2009 (XP002727455) (& Chinese Science Bulletin Press China, vol. 54, No. 9, 2009, pp. 1626-1629) Abstract.
Ma et al., "One-step synthesis of chstine-coated gold nanoparticles in aqueous solution," Colloids and Surfaces, Physicachemical and Engineering Aspects, vol. 317, No. 1-3, 2007, pp. 229-233 (XP022482563).
Sarangi, S. et al., "Strong UV absorption and emission from L-cysteine capped monodispersed gold nanoparticles," Applied Physics Letters, vol. 95, No. 7, 2009, pp. 73109-73109 (XP012122749).
Tvedte, L., et al., "Size-Focusing Synthesis of Gold Nanoclusters with pMercaptobenzoic Acid," The Journal of Physical Chemistry, Mar. 14, 2014 (XP055130121).
Mocanu, Aurora, et al., Colloids and Surfaces A: Physicochemical and Engineering Aspects, vol. 338, Apr. 1-3, 2009, pp. 93-101.
Petean, G.H., et al., Cysteine Mediated Assembly of Gold Nanoparticles, Journal of Optoelectronics and Advanced Materials, 2008, vol. 10. No. 9, pp. 2289-2292.
Dzagli, M.M., et al., Investigation on Gold Nanorods Conjugated with L. Cysteine and Their Applications, The African Review of Physics, 2012, 7:0055, p. 475.
Abraham, Anuji, 1H MAS NMR Study of Cysteine-Coated Gold Nanoparticles, Journal of Physical Chemistry B, 2012, 116 (27), pp. 7771-7775.
Xie, Jianping, Protein-Directed Synthesis of Highly Fluorescent Gold Nanoclusters, Journal American Chemical Society, 2009, 131, pp. 888-889.

* cited by examiner

Figure: 1
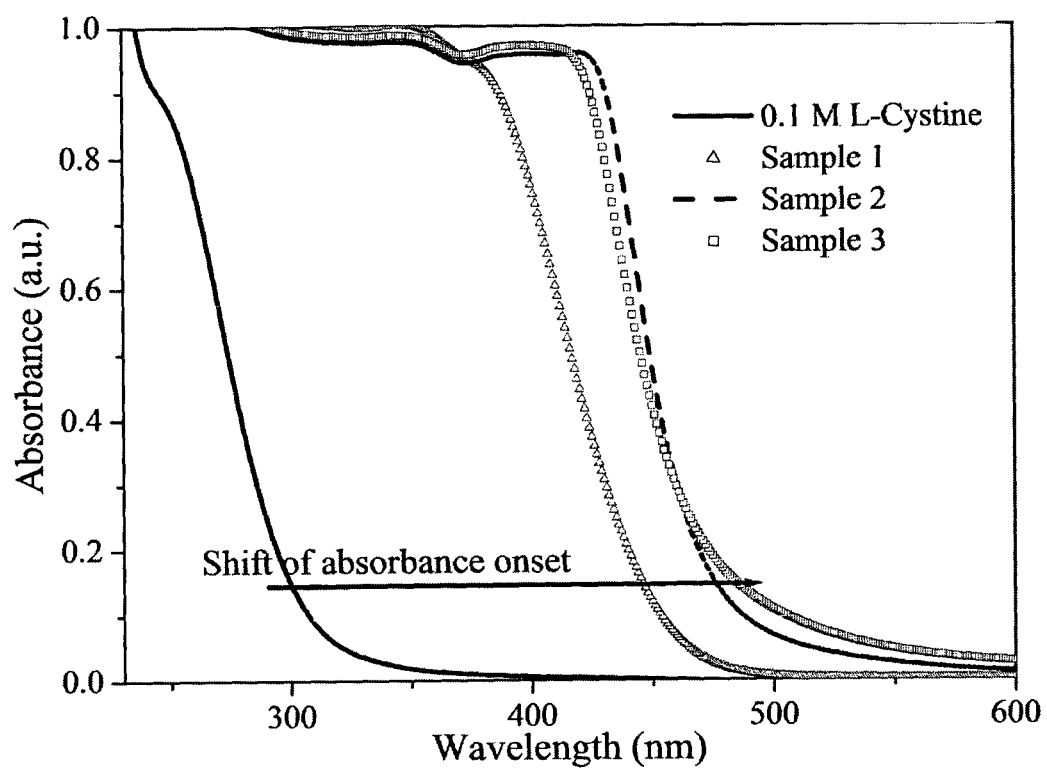

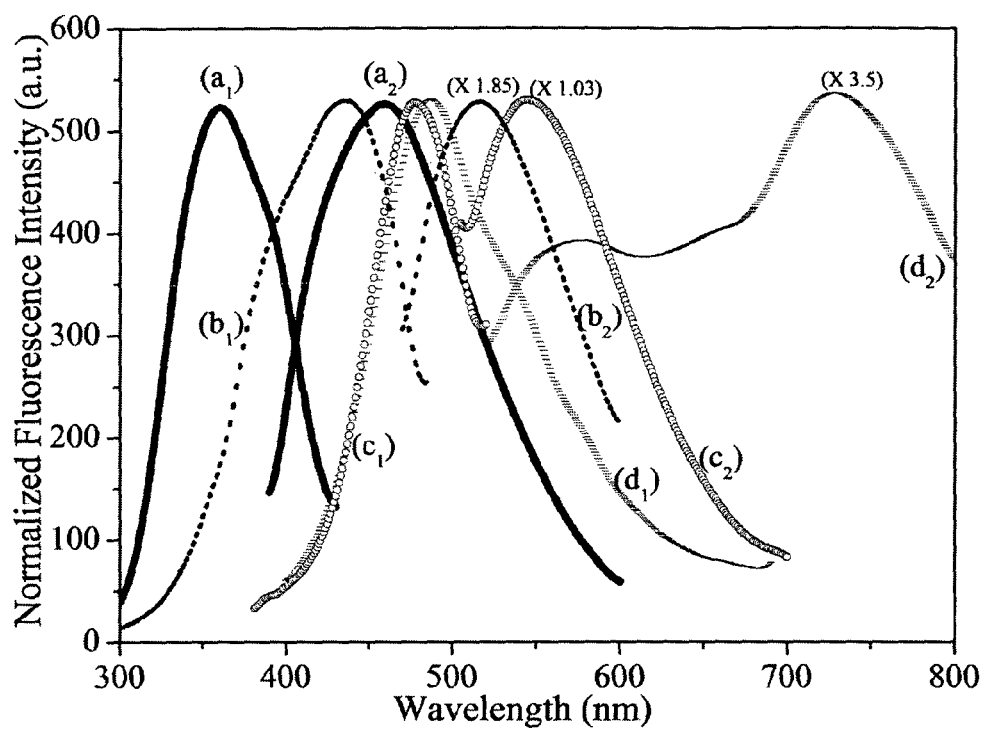
Figure: 2

ONE POT PROCESS FOR THE PREPARATION OF GOLD QUANTUM CLUSTERS

FIELD OF THE INVENTION

The present invention relates to a facile, one-pot process for the synthesis of water dispersive, monodispersible, biocompatible, fluorescent, L-cysteine labeled gold (Au) quantum clusters. Particularly, the present invention provides a facile, one-pot process for the synthesis of water dispersive, monodispersible, biocompatible, fluorescent, L-cysteine labeled gold (Au) quantum clusters of different core size, without addition of any other reducing agent. The present invention also relates to the use of an amino acid molecule, L-cysteine, for the synthesis of water dispersive, biocompatible, a range of fluorescent Au clusters.

BACKGROUND AND PRIOR ART

Usually, noble metals show drastic changes in their electronic properties at nanoscale. The electronic properties of noble metals become more interesting when the size decrease to the extent where it would be comparable to the Fermi wavelength of an electron. Such small size regime is called metal clusters, where the free electrons are confined relative to the Fermi wavelength in the conduction band. These metal clusters composed of few atoms to few tens of atoms and exhibit molecule like, size dependent properties where the valence and conduction bands show further discritization. Excitation of electrons from valence band (filled $5d^{10}$) to the conduction band ($6sp^1$) leads to a strong size dependent fluorescence emission in a range that can extend from the visible to the near-infrared. The synthesis of Au QCs with different core sizes have been reported recently, where the mass spectroscopy, especially, MALDI-TOF was ideally used as a major characterization tool.

In the past decade, researchers have reported multiple step synthesis of different core size of Au QCs employing various capping and reducing agents where most of them are either bulky (like protein or polymers) and/or non-biocompatible which limits their application in biological fields. While Au has been tried, Ag being less stable, gets oxidized and therefore is not very attractive for applications similar to Au.

In other prior arts, alkane thiols are used, which is not recommended, especially for medical applications.

The assembly of gold nanoparticles in presence of semi-essential amino acid such as cysteine for biomedical applications is reported in the art.

Aurora Mocanu et al. in Colloids and Surfaces A: Physicochemical and Engineering Aspects vol 338, 1-3, April 2009, Pgs 93-101 discloses preparation of gold nanoparticles in aqueous dispersions, using sodium citrate as reduction agent, and their interaction with L-cysteine. Further preparation of citrate capped gold nanoparticles of controlled size in aqueous solution and their interaction with L-cysteine is reported by Petean I. in Journal of optoelectronics and advanced materials; 2008, vol. 10, no. 9, pp. 2289-2292.

The gold nanorods conjugated with I-cysteine and their applications" is disclosed by M. M. Dzaglil in the *African Review of Physics* (2012) 7:0055 475. (Additionally $^1$H MAS NMR study of cysteine-coated gold nanoparticles is described in *J. Phys. Chem.* B, 2012, 116 (27), pp 7771-7775 by Anuji Abraham.

Further KR20040060357 discloses a substrate for biosensor and a method for preparing thereof. The substrate for biosensor comprises a solid substrate with one side covered with a metal thin layer; a self-assembled peptide on the metal thin layer of the solid substrate through the cysteine residue in the end; a protein bound to the peptide and having specificity to the invariable region of an antibody; and the antibody bound with the protein, wherein the metal thin layer is composed of gold, silver, copper or white gold; the peptide consists of 5 to 25 amino acids; and the solid substrate is treated with mercaptoethanol solution or mercaptopropionic acid solution.

Zheng and Ying in J. AM. CHEM. SOC. 2009, 131, 888-889 titled "Protein-Directed Synthesis of Highly Fluorescent Gold Nanoclusters" disclose gold nano clusters of a single size, ~25 atoms, which emit red fluorescence, prepared by using $HAuCl_4$, NaOH and a large protein, Bovine Serum Albumin (BSA). Further, the process is a 12 hour reaction to synthesize the nano clusters.

Currently the challenge lies in providing a process to synthesize water dispersive, biocompatible and a range of Au QCs core size population with different emissions, especially, using small, biocompatible non-bulky molecules. Actually, the tuning of the size of Au QCs core, specially using small biomolecule, is a very difficult and quite tricky task.

Moreover, there is no report on the synthesis of small non-bulky and non-essential amino acid molecule conjugated Au QCs so far, wherein amino acid itself provides the site for sequestration of gold ions and plays the role as both reducing and stabilizing/capping agent. Therefore cost-effective, industrially viable and environmental friendly process for the synthesis of water dispersible, highly biocompatible and fluorescent non-bulky amino acid capped or conjugated metal quantum clusters with a range of core size for biomedical applications is highly desirable, which obviates use of any toxic materials.

OBJECT OF INVENTION

The main object of the present invention is to provide a facile, one-pot process for the synthesis of water dispersive, monodispersible, biocompatible, fluorescent, L-cysteine labeled gold (Au) quantum clusters. Another objective of the present invention is to provide a facile, one-pot process for the synthesis of water dispersive, monodispersible, biocompatible, fluorescent L-cysteine labeled gold (Au) quantum clusters of different core size, without addition of any other reducing agent.

One more object of the invention is to provide the facile and one pot synthesis of a small non-bulky amino acid molecule i.e. L-cysteine labeled Au QCs, which is water dispersible, highly biocompatible and fluorescent.

SUMMARY OF THE INVENTION

Accordingly, the present invention provides a facile one-pot process for the synthesis of fluorescent L-cysteine labeled gold (Au) quantum clusters (QCs) of different core size, without addition of any other reducing agent, wherein the process comprises;
  a) mixing a solution of a gold salt with a solution of L-cysteine, followed by the addition of a base, to obtain brown coloured reaction mixture; and
  b) allowing said reaction mixture to stand at ambient temperature ranging between 20-35° C. for a period ranging between 5 10 min for complete reduction of gold ions to obtain L-cysteine labeled gold (Au) quantum clusters.

In an embodiment of the present invention L-cysteine labeled gold (Au) quantum clusters (QCs) are water dispersive, monodispersible, biocompatible.

In one embodiment of the present invention the gold salt used is chloroauric acid ($HAuCl_4$).

In another embodiment of the present invention the concentration of chloroauric acid is in the rage of 0.005 to 0.01M.

Still in another embodiment of the present invention the concentration of L-cysteine solution is in the range of 0.05-0.1M.

Still in another embodiment of the present invention the base is selected from the group consisting of NaOH, KOH, $K_2CO_3$, $Na_2CO_3$, $NaHCO_3$.

Still in another embodiment of the present invention the concentration of NaOH is about 0.1M.

Still in another embodiment of the present invention the gold clusters size is less than 2 nm.

Still in another embodiment of the present invention the gold-quantum-clusters comprise less than 100 atoms of gold metal.

Still in another embodiment of the present invention gold-quantum clusters show differently fluorescing from blue to red according to their size.

BRIEF DESCRIPTION OF THE DRAWINGS

FIG. 1 depicts UV-Vis spectra of L-cysteine and L-cysteine labeled Au QCs.

FIG. 2 depicts Normalized fluorescence excitation (1) and emission spectra (2) for L-cysteine only (-, Solid line), sample 1 ( . . . , Dotted line), sample 2 (o, circle), sample 3 ( - - - Dashed line). Spectra b, c and d were multiplied by 1.85, 1.03 and 3.5 respectively, for clarity.

ABBREVIATIONS

Au QC: Gold Quantum Clusters

Definitions

The term "water dispersible" used in the specification defines the clusters are in suspension form in water and can be easily reconstituted.

The term "biocompatible" defines the ligand used is a FDA approved drug. L-cysteine is a non-essential amino acid i.e. human body can synthesize sufficient L-cysteine to meet its requirements.

The cluster obtained is "mono dispersible" means size of cluster is controlled within a narrow range. The as-obtained Au QCs do not have broad and multiple peaks in the fluorescence spectra. Generally, the broad and multiple peaks in the fluorescence spectra lead to the synthesis of polydisperse Au QCs.

DETAILED DESCRIPTION OF THE INVENTION

The invention will now be described in detail in connection with certain preferred and optional embodiments, so that various aspects thereof may be more fully understood and appreciated.

The present invention provides tunable process for the preparation of water dispersive, biocompatible, fluorescent L-cysteine labeled gold (Au) quantum clusters having different core sizes, without using any toxic reactants.

The present invention provides L-cysteine labeled Au QCs which is biocompatible and water dispersive having tunable fluorescence properties. The invention provides the facile, one pot synthesis of L-cysteine labeled Au QCs comprising the steps of:

a) mixing a solution of a gold salt with a solution of L-cysteine, followed by the addition of a base, to obtain brown coloured reaction mixture; and b) allowing said reaction mixture to stand at ambient temperature for complete reduction of gold ions to obtain Au QCs.

According to the process, gold solution is chloroauric acid $HAuCl4$, wherein the concentration of gold solution ranges from 0.005-0.01M, and volume ranges from 0.1-20 milliliters (ml), while the volume of L-cysteine solution used is in the range of 1-5 ml having concentration in the range of 0.05-0.1M.

The base employed in the process is selected from the group consisting of NaOH, KOH, $K_2CO_3$, $Na_2CO_3$, $NaHCO_3$, preferred base is NaOH with concentration of about 0.1M, and used in the range of 200-600 µl.

The ambient temperature is maintained in between 20-35° C., preferably 25° C.

Further the synthesized quantum clusters contain less than 100 atoms of gold metal, wherein the Au clusters having the sizes less than 2 nm.

The process of formation of L-cysteine labeled Au QCs disclosed results in the formation of the QCs within few minutes. The process of synthesis is completed in 5 minutes.

The invention provides facile, one pot process for the synthesis of L-cysteine labeled Au QCs comprises:

a) mixing of 0.01 M $HAuCl_4$ and 0.1M L-cysteine solutions followed by the addition of 0.1 M NaOH, to obtain brown coloured reaction mixture; and b) allowing said reaction mixture to stand for 5 min at 25° C. for complete the reduction of gold ions to obtain Au QCs.

The instant L-cysteine labeled Au QCs having different core sizes are characterized by using UV-vis spectroscopy and fluorescence spectroscopy.

EXAMPLES

Following examples are given by way of illustration therefore should not be construed to limit the scope of the invention.

Example 1

$10^{-2}$ M HAuCl4 and $10^{-1}$ M L-cysteine solutions were mixed following the addition of $10^{-1}$ M NaOH, as shown in Table 1, to prepare 3 samples without addition of any other reducing agent, catalyst or template. Immediately after the addition, the color of mixture was turned to red first and then brown. The 3 sample mixture of solutions was left at 250 C for 5 min to complete the reduction process of gold ions into the Au cluster. The suspension as such for each sample was used for further characterization.

TABLE 1

Composition of various L-cystines labeled Au clusters.

| Sample Name | Volume of $10^{-1}$ M L-cystine (ml) | Volume of $10^{-2}$ M HAuCl$_4$ (ml) | Volume of $10^{-1}$ M NaOH (μl) |
|---|---|---|---|
| Sample1 | 2 | 0.5 | — |
| Sample2 | 2 | 8 | 250 |
| Sample3 | 2 | 10 | 500 |

UV-Vis spectra of sample 1 Au QCs (cf FIG. 1) showed the broad and strong absorption in the UV range starting from ~490 nm with the absence of surface plasmon resonance peak (520 nm) that indicated the presence of Au QCs having the sizes smaller than ~2 nm. The spectra of gold QCs samples were quite different from the spectrum of pure L-cysteine solution. The shift of absorbance onset to the longer wavelength showed the synthesis of Au QCs with larger core sizes. Further, photoluminescence properties were studied by fluorescence spectroscopy and confirmed the synthesis of Au cluster with various core sizes. The emission peak position for fluorescent Au clusters depends on the size of the Au QC core. According to the spherical Jellium model, Au QCs with larger core size emit at longer wavelengths (e.g., UV (Au$_5$), blue sample 1(Au$_8$), green sample 2(Au$_{13}$), and red sample 3 (Au$_{25}$) emission. Fluorescence excitation and emission spectra for all samples were demonstrated in FIG. 2. The shift in fluorescence excitation and emission spectrum peaks for different Au QCs suspension exhibits the synthesis of Au QCs with different core sizes.

ADVANTAGES OF INVENTION

1. One pot simple route of synthesis.
2. The process does not require use of other reducing agent, catalyst or template.
3. The process involves the use of small, biocompatible and non-toxic molecule, like L-cysteine which adds the key advantage of use of the L-cysteine capped Au QCs for biological systems.
4. The process allows the synthesis of different core size Au QCs with various emissions.

We claim:

1. A facile one-pot process for the synthesis of fluorescent L-cysteine labeled gold (Au) quantum clusters (QCs) of different core size, the process consisting essentially of;
    a) mixing a solution of a gold salt with a solution of L-cysteine, followed by the addition of a base, to obtain brown coloured reaction mixture; and
    b) allowing said reaction mixture to stand at ambient temperature ranging between 20-35° C. for a period ranging between 5-10 min for complete reduction of gold ions to obtain L-cysteine labeled gold (Au) quantum clusters.

2. The one-pot process according to claim 1, wherein L-cysteine labeled gold (Au) quantum clusters (QCs) are water dispersive, monodispersible, biocompatible.

3. The one-pot process according to claim 1, wherein the gold salt used is chloroauric acid (HAuCl$_4$).

4. The one-pot process according to claim 3, wherein the concentration of chloroauric acid is in the range of 0.005 to 0.01M.

5. The one-pot process according to claim 1, wherein concentration of L-cysteine solution is in the range of 0.05-0.1M.

6. The one-pot process according to claim 1, wherein the base is selected from the group consisting of NaOH, KOH, K$_2$CO$_3$, Na$_2$CO$_3$, NaHCO$_3$.

7. The one-pot process according to claim 6, wherein the concentration of NaOH is about 0.1M.

8. The one-pot process according to claim 1, wherein the gold clusters' size is less than 2 nm.

9. The one-pot process according to claim 1, wherein the gold-quantum clusters comprise less than 100 atoms of gold metal.

10. The one-pot process according to claim 1, wherein gold-quantum clusters show differently fluorescing from blue to red according to their size.

* * * * *